United States Patent [19]

Vescovini et al.

[11] Patent Number: 5,120,302
[45] Date of Patent: Jun. 9, 1992

[54] BLOOD CONTAINER FOR MEDICAL APPARATUS

[75] Inventors: Pietro Vescovini, Medolla; Nicola Ghelli, S. Pietro in Casale, both of Italy

[73] Assignee: Dideco, S.p.A., Mirandola, Italy

[21] Appl. No.: 549,473

[22] Filed: Jul. 6, 1990

[51] Int. Cl.⁵ .......................... A61M 37/00
[52] U.S. Cl. ............................ 604/4; 604/5; 604/6; 604/405; 128/DIG. 3; 422/47
[58] Field of Search ................ 220/669; 222/547, 630; 422/47; 128/DIG. 3; 604/405, 406, 4-6

[56] References Cited

U.S. PATENT DOCUMENTS

| | | | |
|---|---|---|---|
| 4,058,369 | 11/1977 | Bentley et al. | 128/DIG. 3 X |
| 4,282,180 | 8/1981 | Raible | 128/DIG. 3 X |
| 4,428,743 | 1/1984 | Heck | 604/4 |
| 4,440,723 | 4/1984 | Gordon | 128/DIG. 3 X |
| 4,642,089 | 2/1987 | Zupkas et al. | 128/DIG. 3 X |
| 4,664,682 | 5/1987 | Monzen | 604/406 X |

Primary Examiner—Robert A. Hafer
Assistant Examiner—Kerry Owens
Attorney, Agent, or Firm—P. C. Richardson; L. C. Akers; A. Passman

[57] ABSTRACT

A blood container comprises a generally cylindrically shaped outer housing (11) having an upper portion, a lower portion and a bottom portion which declines downwardly to an outlet 3. A generally cylindrically shaped filter 2 is enclosed concentrically within the upper portion of outer housing for receiving blood at the top thereof and discharging filtered blood at the wall and base of the filter. A generally cylindrically shaped inner housing (4) extending from the base of the filter to the bottom portion of the outer housing. The container particularly includes means (5, 9, 9a, 9b, 11) for directing and restricting the flow of blood from the base of the filter for a gradual and smooth descent to the outlet which avoids the creation of bubbles and avoids any blood cell damage.

7 Claims, 2 Drawing Sheets

BLOOD CONTAINER FOR MEDICAL APPARATUS

BACKGROUND OF THE INVENTION

The invention relates to a blood container known as a cardiotomy reservoir for medical apparatus.

Medical apparatus, for example, of cardiotomies and oxygenators are well-known which include a blood container which has a filter which receives the inflowing blood. In these containers it is important that the blood flows through the filter without stagnating or coagulating to avoid reducing filtration effectiveness and lowering the physiological properties of the blood. This requirement leads to containers in which the blood can be kept at a distinctly lower level than the base of the filter, in a reservoir which readily provide a good read out scale of the free surface level and blood volume in order to facilitate the operator in his functions. In such containers the blood drops by gravity from the level of the base of the filter to the level of the underlying free surface, and this consequently causes a severe danger of formation of bubbles and microemboli and of blood cell damage.

An object of the present invention is to provide a blood container for medical apparatus in which the blood flows through the filter and descends gradually and smoothly toward the underlying free surface and outlet in such a manner as to ensure the absence of bubbles and provide assurances against any blood cell trauma.

SUMMARY OF THE INVENTION

The proposed object is achieved in accordance with the present invention by a blood container comprising a generally cylindrically shaped outer housing having an upper portion, a lower portion and a bottom portion which declines downwardly to an outlet; a generally cylindrically shaped filter enclosed concentrically within the upper portion of the upper housing for receiving blood at the top thereof and discharging filtered blood at the wall and base thereof; and a generally cylindrically shaped inner housing extending from the base of the filter to the bottom portion of the outer housing. The container includes by means for directing and restricting the flow of blood from the base of the filter for a gradual and smooth descent to the outlet. In a preferred embodiment, the flow directing means comprises a plurality of horizontal radial steps formed in the bottom portion; a plurality of radial baffles extending vertically from the bottom portion, an arcuate partition extending from the inner housing above the outlet of the inner housing; and a plurality of flutes extending radially from the inner housing.

The proposed object is equally achieved by a second embodiment wherein the flow directing means comprises the inner housing further comprises a partially annular duct for directing blood from the base of the filter to the upper end of the declined bottom portion of the outer housing and a plurality of radial partitions extending vertically generally between the inner housing and the outer housing for restricting the flow path between the outer housing and the inner housing.

DETAILED DESCRIPTION OF THE INVENTION

Further characteristics and advantages will become apparent from the description of two preferred but not exclusive embodiments of the invention, illustrated only by way of non-limiting example in the accompanying drawings, wherein.

Figure 1:
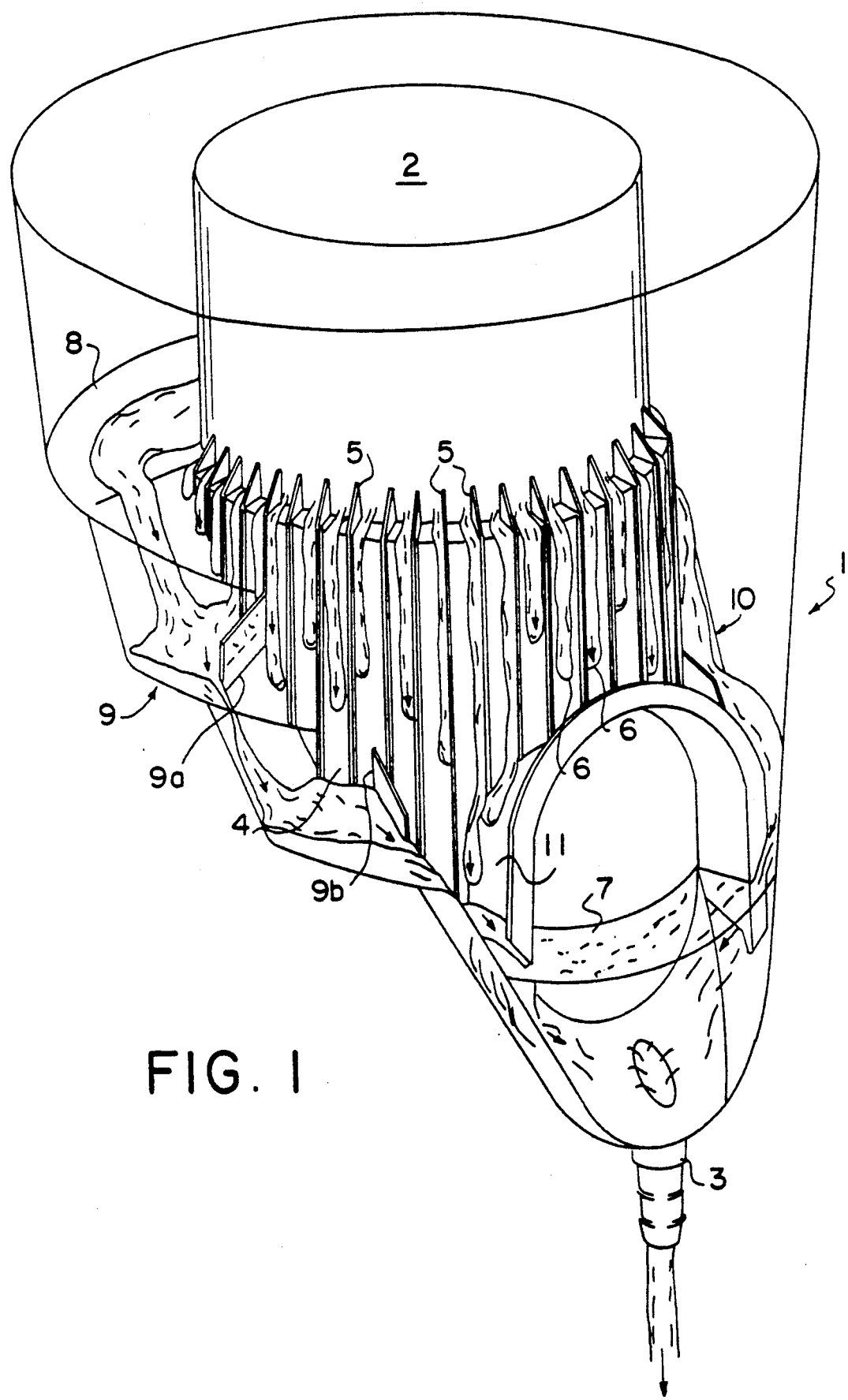
FIG. 1 is a front perspective view of a first embodiment of the invention.

With reference to FIG. 1, a blood container comprises a generally cylindrically shaped outer housing 1 enclosing a concentric filter 2 within the upper portion thereof, and which has a bottom portion which declines downwardly to an outlet 3. The container includes an inlet (not shown) for receiving blood within the interior of the filter. The outer housing is preferably formed of a suitable transparent plastic material. The container includes a generally cylindrically shaped inner housing 4 which extends from the base of the filter to the bottom portion of the container. The inner housing 4 is provided with radial ridges or flutes 5 which define a plurality of ducts for the gravity descent of the blood in streams 6 which adhere to the wall and flow toward the free blood level surface 7 proximate to the bottom portion of the container. A partially annular planar surface 8 is provided near the base of the filter 2 and forms the uppermost surface of the declined bottom portion of the housing. The declined bottom continues downwardly via a series of generally horizontal radial steps 9 and 10 which are interconnected by sloping surfaces and which tend to help control the gradual descent of the blood. The bottom portion further includes a series of ridges or baffles 9a and 9b which extend vertically from the bottom portion and extend radially from the inner housing 4 to form a narrow opening adjacent to the outer housing to further provide a gradual and smooth descent of the blood flow.

In this manner the blood which flows out of the filter 2 and collects on the planar surface 8, and the blood conveyed by the ducts defined by the flutes 5 on the cylindrical surface of the inner housing 4, descends along the radial steps 9 and 10 and sloping surfaces, retarded by the partially restricting baffles 9a and 9b and is forced thereby to flow adjacent to the wall of the outer housing; the blood is further slowed down by an arcuate partition 11 which limits the vertical drop of the blood along flutes 5 above the outlet 3 and allows the blood to flow only at a narrow port adjacent to the surface of the declined bottom.

The container of the invention provides the desired advantages in which the blood quickly and smoothly passes through the filter and descends gradually and smoothly to the free surface. An operator can easily keep the free surface 7 of the blood well below the base of the filter 2 by means of an appropriate choice of the operating parameters. A blood level or blood volume scale indicating the level of the free surface 7, can be provided on the transparent housing above the outlet to further facilitate the utility of the container. The smooth gradual gravity descent of the blood toward the free surface 7 and the outlet occurs by virtue of the described system of ridges and baffles which divide the entire flow of blood into small streams which flow in contact with the walls of the housing, so as to avoid the forming of bubbles and any blood cell damage.

A further variation of the described embodiment can be provided in which the flutes 5 extend radially from the inner housing 4 to a position closely adjacent the outer housing 1; thereby providing the function of both the flutes 5 and the baffles 9a and 9b to direct and control the flow of blood for a gradual and smooth descent to the free surface 7.

Figure 2:
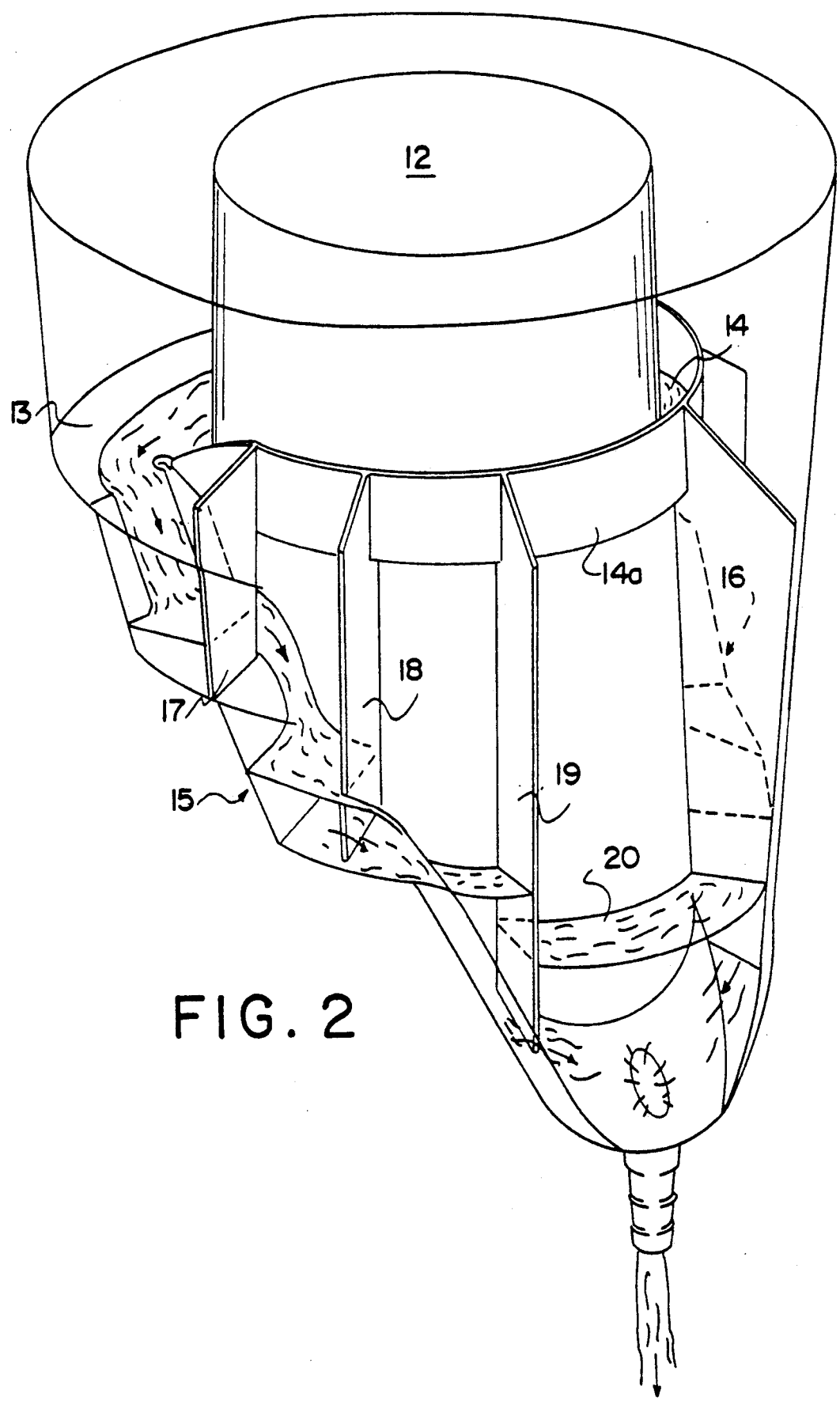
FIG. 2 is a front perspective view of a further embodiment of the invention.

FIG. 2 illustrates a second embodiment of a blood container which comprises a cylindrically shaped outer housing and a steeped sloping bottom portion 13, 15 and 16 which declines downwardly similarly to the outer housing of FIG. 1. The housing encloses a concentric filter 12 in the upper portion thereof and for receiving blood from an inlet (not shown) and discharging blood from the wall of the filter. The container includes a generally cylindrically shaped inner housing which extends from the base of the filter to the bottom portion of the outer housing. The bottom portion includes the partially annular planer surface 13 at the uppermost part thereof near the base of the filter for receiving flow directly from a portion of the filter. The inner housing includes a partially annular duct formed by a surface 14 and a flange 14a which partially encircles the base of the filter and directs the remainder of the flow from the filter onto surface 13. The container includes radial partitions 17, 18 and 19 extending vertically from the bottom portion between the inner housing and the outer housing and having alternate passageways near the inner and outer housing walls for directing flow to the free surface 20 and the outlet.

The blood flow thus descends quickly and completely through the filter 12; and then partially directly and partially by duct 14 and 14a onto the surface 13; and then along the stepped declined sloped bottom portion 15, 16 and 17 and is then directed and retarded by the partitions 17, 18 and 19 alternately along the inner wall and along the outer wall to smoothly control the descend of the blood in a manner which avoids the formation of bubbles or microemboli and blood cell damage.

What is claimed is:

1. A blood container comprising:
   a generally cylindrically shaped outer housing having a wall of transparent material defining an upper portion and a lower portion, the outer housing including a bottom portion which declines downwardly to an outlet;
   a generally cylindrically shaped filter enclosed concentrically within the upper portion of said upper housing for receiving blood at the top thereof and discharging filtered blood at an annular planar surface which extends to the wall for permitting the discharged filtered blood to descend along the wall wherethrough the filtered blood is visible during decent to the base thereof;
   a generally cylindrically shaped inner housing extending from the base of said filter to the bottom portion of said outer housing; and
   means for directing and restricting the flow of blood from the base of said filter for a gradual and smooth descent to said outlet.

2. A blood container according to claim 1 wherein said flow directing means comprises a plurality of horizontal radial steps formed in the bottom portion of said outer housing.

3. A blood container according to claim 1 wherein said flow directing means comprises a plurality of radial baffles extending generally vertically from the bottom portion of said outer housing for restricting the flow path between said outer housing and said inner housing.

4. A blood container according to claim 1 wherein said flow directing means comprises a plurality of flutes extending radially from said inner housing.

5. A blood container according to claim 1 wherein said flow directing means includes an arcuate partition extending from said inner housing and above the outlet of said outer housing.

6. A blood container according to claim 2 wherein said flow directing means comprises a plurality of radial baffles extending vertically from the bottom portion; an arcuate partition extending from said inner housing above the outlet of said outer housing; and a plurality of flutes extending radially from said inner housing.

7. A blood container according to claim 2 wherein said inner housing further comprises a partially annular duct for directing blood from the base of said filter to the upper end of the declined bottom portion of said outer housing and a plurality of radial partitions extending vertically generally between said inner housing and said outer housing for restricting the flow path between said outer housing and said inner housing.

* * * * *